US008674315B2

(12) United States Patent
Vija et al.

(10) Patent No.: US 8,674,315 B2
(45) Date of Patent: Mar. 18, 2014

(54) METHOD AND APPARATUS FOR USING IMAGE CUMULATIVE DISTRIBUTION FUNCTION FOR TOMOGRAPHIC RECONSTRUCTION QUALITY CONTROL

(75) Inventors: Alexander Hans Vija, Evanston, IL (US); Amos Yahil, Stony Brook, NY (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 754 days.

(21) Appl. No.: 12/944,871

(22) Filed: Nov. 12, 2010

(65) Prior Publication Data

US 2012/0119096 A1 May 17, 2012

(51) Int. Cl.
*G01T 1/24* (2006.01)

(52) U.S. Cl.
USPC ............... 250/370.08; 250/363.04; 378/4; 382/131; 382/154

(58) Field of Classification Search
USPC ............. 250/370.08, 363.04; 378/4; 382/154, 382/131
See application file for complete search history.

(56) References Cited

U.S. PATENT DOCUMENTS

| 5,164,993 | A  | * | 11/1992 | Capozzi et al. | 382/132 |
| 6,687,400 | B1 | * | 2/2004  | Szeliski       | 382/168 |
| 6,792,439 | B2 | * | 9/2004  | Schmidt        | 708/250 |
| 7,034,310 | B2 |   | 4/2006  | Turner         |         |
| 7,085,405 | B1 |   | 8/2006  | Levkovitz et al. |       |
| 8,050,476 | B2 | * | 11/2011 | Dentinger      | 382/131 |
| 2003/0059096 | A1 | * | 3/2003 | Dekel et al.   | 382/131 |
| 2003/0065691 | A1 | * | 4/2003 | Schmidt        | 708/250 |
| 2005/0013471 | A1 | * | 1/2005 | Snoeren et al. | 382/131 |
| 2005/0254721 | A1 | * | 11/2005 | Hagiwara      | 382/260 |
| 2008/0270465 | A1 |   | 10/2008 | Vija et al.   |         |
| 2009/0110255 | A1 |   | 4/2009  | Vija et al.   |         |

OTHER PUBLICATIONS

Puetter, Richard C. and Yahil, Amos, The Pixon Method of Image Reconstruction, Astronomical Data Analysis Software and Systems VIII ASP Conference Series, vol. 172, 1999, pp. 307-316.
Wesolowski, Carl. A. et al., Improved lesion detection from spatially adaptive, minimally complex, Pixon reconstruction of planar scintigraphic images, Computerized Medical Imaging and Graphics vol. 29, 2005, pp. 65-81.

* cited by examiner

*Primary Examiner* — David Porta
*Assistant Examiner* — Djura Malevic
(74) *Attorney, Agent, or Firm* — Peter Kendall (57) ABSTRACT

Methods and apparatuses for quality control in image space for processing with an input data set are disclosed. A method includes providing an image object, including multiple voxels, and an input data set. A data model is determined from the image object. A cumulative distribution function (CDF) for the input data set is determined from the data model and the input data set based on a plurality of projections. The CDF is transformed to an image cumulative distribution function (ICDF) in object space. The ICDF represents a number of standard deviations associated with each voxel of the image object. The output of the ICDF is displayed. A nuclear imaging system and a computer readable storage medium are also disclosed. Techniques disclosed herein facilitate efficient quality control for tomographic image reconstruction.

23 Claims, 5 Drawing Sheets

METHOD AND APPARATUS FOR USING IMAGE CUMULATIVE DISTRIBUTION FUNCTION FOR TOMOGRAPHIC RECONSTRUCTION QUALITY CONTROL

BACKGROUND

Tomographic reconstruction technology enables three-dimensional imaging of volumes for a variety of applications, e.g., medical imaging. In some nuclear imaging applications, a radioactive substance is administered to a patient, and emitted radiation is detected with a detector system. An imaging detector detects the γ-radiation emitted from the patient and provides the data set to an image reconstruction unit, which computes an image object, e.g., a three dimensional (3D) image object, on the basis of the data set. A well-known objective statistical measure for modeling Poisson-distributed radiation counts, which is well behaved at low counts, is the Poisson cumulative distribution function (Poisson CDF). Because the CDF is piecewise constant with discontinuities at integer points, a random component may be added to provide a modified Poisson CDF (MCDF). The MCDF, although useful for its continuity and lack of inter-pixel correlation, is susceptible to sensitivity problems because it is processed one projection at a time. Furthermore, the MCDF is computed in data space (not image space) and thus does not provide meaningful insights into disparities between a predicted model and actual results in image space.

SUMMARY

In some embodiments, a method for quality control in image space for processing with an input data set includes providing an image object (e.g., a 3D image object) and an input data set. The image object includes multiple voxels. A data model is determined from the image object. A cumulative distribution function (CDF) for the input data set is determined from the data model and the input data set based on a plurality of projections. The CDF is transformed to an image cumulative distribution function (ICDF) in object space (image space). The ICDF represents a number of standard deviations associated with each voxel of the image object. An output of the ICDF is displayed.

In some embodiments, a computer readable storage medium has instructions stored on it. When executed by a processor, the instructions cause the processor to perform the operations of the method for quality control in image space for processing with an input data set described above.

In some embodiments, a nuclear imaging device includes a detector unit, a tomographic reconstruction unit, an ICDF module, and an output port. The detector unit is configured to detect radiation emitted from within a detecting area and provide an input data set indicative of the detected radiation. The tomographic reconstruction unit is configured to provide an image object using the input data set. The image object includes a plurality of voxels. The ICDF module is configured to transform a cumulative distribution function (CDF) for the input data set in data space to an image cumulative distribution function (ICDF) in object space (image space). The ICDF represents a number of standard deviations associated with each voxel of the image object. The output port is configured for outputting the image object and the ICDF.

BRIEF DESCRIPTION OF THE DRAWINGS

The following will be apparent from elements of the figures, which are provided for illustrative purposes and are not necessarily to scale.

DETAILED DESCRIPTION

This description of the exemplary embodiments is intended to be read in connection with the accompanying drawings, which are to be considered part of the entire written description.

Figure 1:
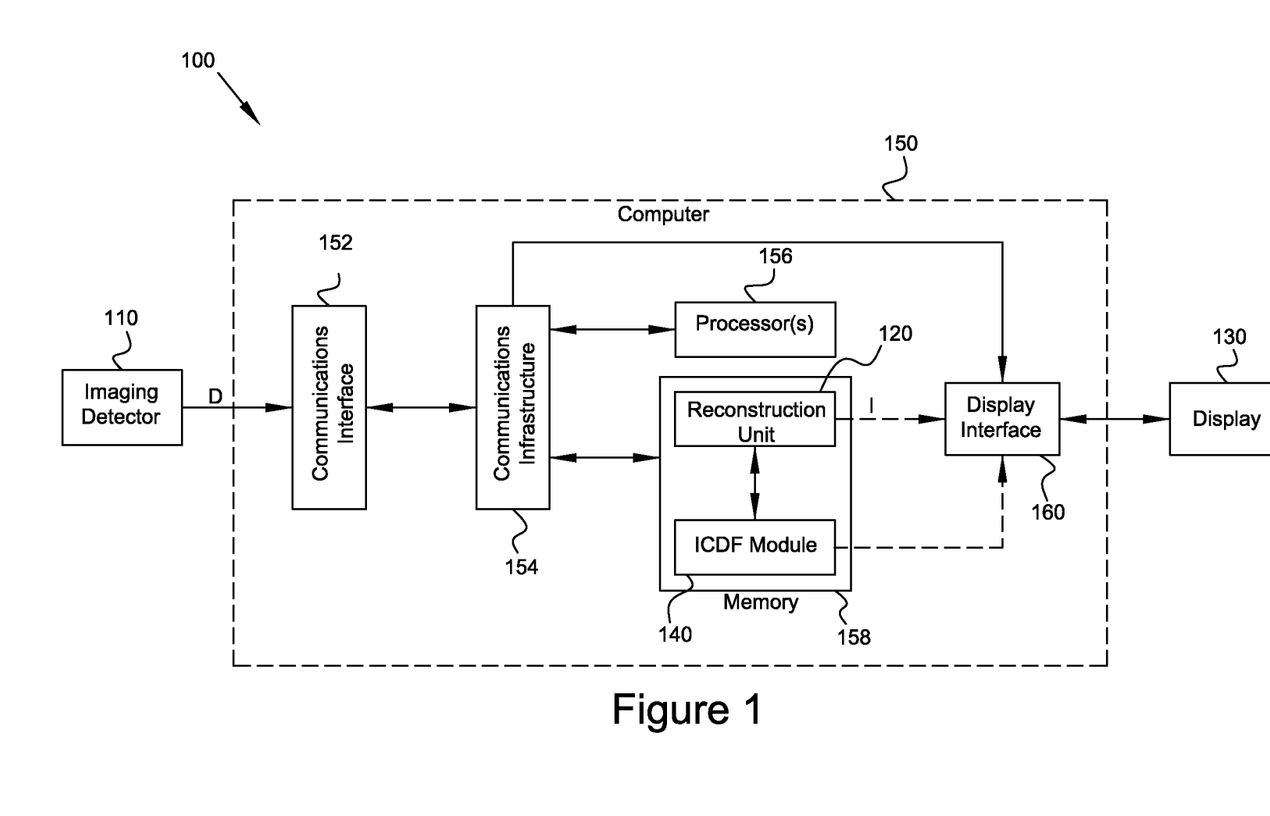
FIG. 1 is a block diagram of a nuclear imaging system.

FIG. 1 shows a nuclear imaging system 100 comprising an imaging detector 110, an image reconstruction unit 120, a display (output port) 130, and an image cumulative distribution function (ICDF) module 140. The image reconstruction unit 120 and ICDF module 140 may be components of a computer system 150, which provides a computing platform to process data from the imaging detector 110. Computer system 150 is described in greater detail below after description of FIGS. 2-6.

The image reconstruction unit provides a reconstructed image object I using a known tomographic reconstruction algorithm, e.g., an algorithm described in U.S. Pat. Pub. No. 2008/0270465, "NNLS Image Reconstruction" by Vija et al., or U.S. Pat. Pub. No, 2009/0110255, "Reconstructing a Tomographic Image" by Vija et al., the contents of which references are hereby incorporated herein in their entirety. The image object I may be provided to display 130 via communications infrastructure 154 and display interface 160, or it may be provided directly to display interface 160 (as shown by dashed lines in FIG. 1). As used herein, an "object" or "image object" is defined in an object space (also referred to as image space) and is a reconstruction of a data set D measured in a data space. The object space is the space in which the result of the image reconstruction is defined and which corresponds to the volume that was imaged using the nuclear imaging system 100 (the input object provided to the nuclear imaging system 100). The image object may be a three dimensional (3D) image object or may have any other dimensionality, e.g., for N-dimensional imaging. Thus, "volume" as used herein may be an N-dimensional volume. Embodiments of the present disclosure are suitable for higher-dimensional imaging in a variety of applications, with some applications described herein relating to medical imaging.

Some tomographic reconstruction algorithms are especially suited for reconstructing an object from a measured data set with a low number of radiation counts and an unavoidable noise contribution. Such data sets are produced, for example, with medical imaging techniques in nuclear medicine, which produce images (e.g., 3D images) of, for example, a functional process in a patient's body by using nuclear properties of matter. Examples of such imaging techniques are Positron Emission Tomography (PET) and Single Photon Computed Tomography (SPECT). For these types of nuclear imaging, a radioactive substance is administered to the patient, and the emitted radiation is detected with a detector system, e.g., with a ring detector for PET or with one or several gamma cameras for SPECT.

The imaging detector 110 of the nuclear imaging system 100 is positioned around or partly around the patient and may be a conventional SPECT or PET detector system. The imaging detector 110 detects the γ-radiation emitted from the patient and provides the data set D to the image reconstruction unit 120, e.g., by way of communications interface 152 and communications infrastructure 154. The image reconstruction unit 120 uses a system matrix H to describe the properties of the nuclear imaging system 100 and uses an iteratively improved data model to calculate the image object I on the basis of the data set D. An image object I, which may be an N-dimensional image object (typically N=3 in medical imaging applications), is then displayed on display 130 using a known volume rendering techniques.

As shown in FIG. 1, object space and data space are related to each other through the nuclear imaging system 100. This relation is modeled by the system matrix H, Thus, for the projection operation, one can use the system matrix H and its transpose $H^T$ to transform objects between object space and data space.

A forward projection projects an input object $I_{object}$ from object space into data space to yield a data model $M_{data}$ of the input object $I_{object}$. The input object $I_{object}$ can be either an estimated object, e.g., an initial image object $I_0$ or a preceding updated object $I_{update}$ in an iterative update process, or any object defined in object space. A forward projection is an application of the system matrix H to an object in object space. The result of a forward projection is a projected object in data space. For example, projecting an estimated image $I_a$ (where a represents a measurement angle) into data space results in a data model $M_i$ of that estimated image:

$$M_i = \sum_\alpha H_{i\alpha} I_\alpha$$

However, the system matrix H is rarely applied as a matrix multiplication. Instead, it is represented as a product of operators:

$$H = H_n \otimes H_{2 \otimes H_1} \otimes \ldots \otimes H_{2 \otimes H_1}$$

Corresponding to the forward projection, the backward projection from the data space into object space can be described as an application of the transpose $H^T$ of the system matrix H:

$$I_\alpha = \sum_i H_{\alpha i} M_i$$

The transpose $H^T$ is also rarely applied as a matrix multiplication. Instead, it is represented as a product of operators:

$$H^T = H_1^{TH \ominus_2^T \ominus^n} \ldots H \underset{n}{\otimes}^T$$

The differences between the values of the measured data set D and those of the data model M are called residuals. In other words, residuals refer to the difference between the counts (e.g., photon counts) displayed or predicted by a processed image object (image) and the actual counts obtained. In some embodiments, residuals are used to assess image quality and/or identify problematic images. The standard deviation of residuals of Poisson-distributed counts depends on the signal strength and therefore varies from one location in an image to another. A well-known, objective statistical measure, which is well behaved at low counts, is the cumulative distribution function (CDF), which is the probability P(count ≤n|m) of obtaining a Poisson count of n or less when the expected Poisson count is m. Because the probability of obtaining exactly k counts (k being a non-negative integer) is $$P(k; m) = \frac{e^{-m} m^k}{k!},$$

the CDF is given by $$CDF(n \mid m) = \sum_{k \leq n} \frac{e^{-m} m^k}{k!}.$$

Embodiments of the present disclosure may use various cumulative distribution functions, with the Poisson cumulative distribution function described herein as an example.

The use of the CDF in image quality assessment is to determine whether a reconstructed tomographic image is consistent with the underlying Poisson distribution of the input counts. Each data pixel i in a slice (e.g., 2D slice) of image data (or each voxel i in data of dimensionality higher than two, e.g., 3D) has an associated predicted count iii, and an observed count $n_i$. For convenience, image objects are described below as 3D image objects, and slices are described as 2D slices, although image objects and slices may have other dimensionalities. 3D images (image objects) may be represented as multiple 2D slices, which may be displayed individually. The term "pixel" is used herein in the context of slices, with the understanding that a pixel may correspond to a voxel of an image object (e.g., a 3D image object). The working hypothesis is that $n_i$ is a random Poisson realization of $m_i$. If this hypothesis is correct, the distribution of the CDF values $p_i$ of the pixels (for various i) will be homogeneously distributed on [0,1] and will be independent from one pixel to the next, i.e., there will be no positional correlation of the values $p_i$.

A technical difficulty in evaluating whether the distribution of the CDF is homogeneous and spatially uncorrelated is due to the fact that Poisson counts can only take on integer values, so the CDF is piecewise constant with discontinuities at integer points. At the discontinuities, the CDF is only bracketed between a lower bound and an upper bound but is otherwise undetermined. To avoid this ambiguity, a random component is added at the discontinuities to provide the following modified Poisson CDF (MCDF):

MCDF(n|m)=CDF(n|m)+[CDF(n+1|m)−CDF(n|m)]
    *RANDOMU(seed), where RANDOMU is a uniform random distribution on the interval [0,1] and seed is a seed value provided to a pseudo-random number generator.

Under the null hypothesis of a correct data model, the MCDF, which is defined in data space, is a continuous homogeneous distribution function, distributed on the interval [0,1]. Also, because the random numbers are chosen independently in each pixel from the uniform distribution in the interval [0,1], the MCDF exhibits no correlation among (between) pixels under the null hypothesis. Violations of the null hypothesis are manifested in the form of statistically significant projected correlations and/or inhomogeneous distribution on the interval [0,1].

Because the MCDF is processed one projection at a time, it is possible for a model to indicate that the null hypothesis is validated (i.e., the model is correct) for each projection and yet yield a problematic image when all the projections are considered together. This problem may occur, for example, if an individual projection lacks sufficient signal to noise ratio (SNR) to result in an indication of an incorrect model via the MCDF. In other words, individual projection angles used to compute the reconstructed tomographic image are less sensitive to tomographic information and may yield a false impression of correctness.

Another challenge associated with the MCDF is that because the MCDF is computed in data space (projection space), disparities identified in data space do not indicate where disparities are in image space. In other words, one may be able to deduce from the MCDF that a problem exists in data space but yet not know where the problem is in image space, which is of direct importance when one wishes to correct an imaging configuration, for example.

Figure 2:
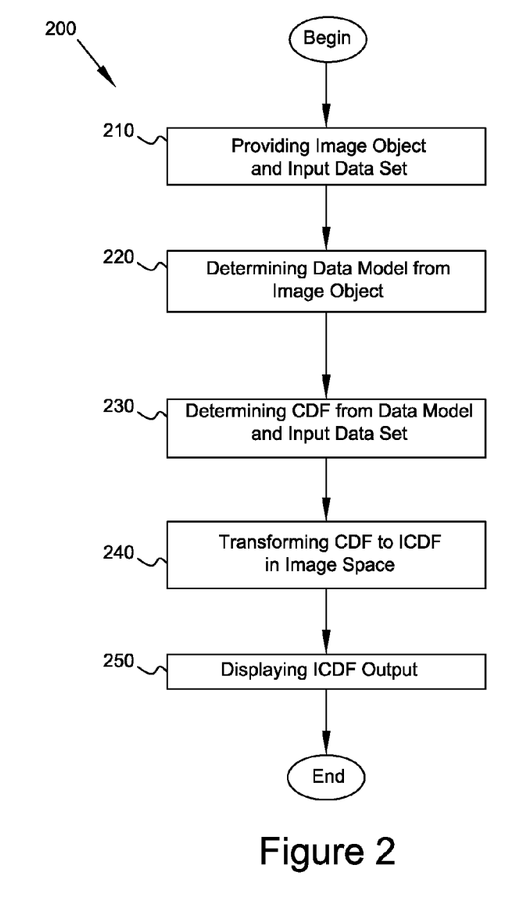
FIG. 2 is a flow diagram of a process in accordance with some embodiments.

FIG. 2 is a flow diagram of a process in accordance with some embodiments. After process 200 begins, an image object and an input data set are provided (see block 210). The image object may include multiple voxels. The image object that is provided may have been reconstructed from the data by various reconstruction approaches. A data model is determined (see block 220) from the image object, e.g., via forward projection. A CDF for the input data set is determined in data space (see block 230) based on a plurality of projections. The CDF (e.g., modified Poisson CDF) is transformed (see block 240) to an image cumulative distribution function (ICDF) in object space (image space). The ICDF represents a number of standard deviations associated with each voxel of the image object. Essentially, the ICDF represents probability in image space in a manner similar to the CDF representing probability in data space. Although the modified Poisson distribution function (MCDF) is described herein as an example, other cumulative distribution functions may be used as well. The output of the ICDF is displayed (see block 250), e.g., on an output port, screen, or other display unit of the nuclear imaging system 100.

Figure 3:
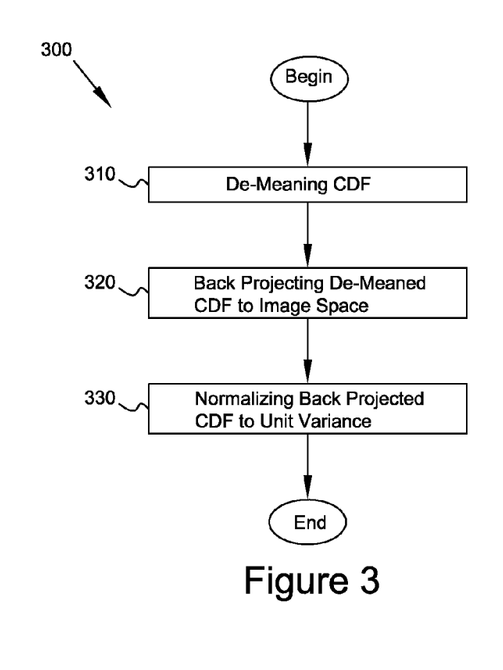
FIG. 3 is a flow diagram illustrating transformation of a cumulative distribution function (CDF) to an image cumulative distribution function (ICDF).

FIG. 3 is a flow diagram illustrating transformation of the CDF to the ICDF. The CDF (e.g., modified Poisson CDF) in data space (projection space) may be transformed to the ICDF in image space (object space) by the ICDF module 140 in the nuclear imaging system 100 of FIG. 1. After process 300 begins, the CDF is de-meaned (see block 310), i.e., processed to remove the mean. The de-meaned CDF is back projected (see block 320) to image space and then normalized (see block 330) to unit variance. In the case of a modified Poisson CDF, because the MCDF is homogeneously distributed on the interval [0,1] under the null hypothesis, the MCDF may be de-meaned by subtracting 0.5 from it. Back projecting the quantity (MCDF−0.5) yields a quantity that has zero mean in image space under the null hypothesis. The variance may be normalized to unit variance by taking advantage of the fact that back projections of different angles (i.e., independent measurements) are statistically independent. For each voxel in an image object, a first back projection (for a first angle) is independent of a second back projection. Thus, the total variance may be estimated by squaring and adding individual angular contributions, i.e., squaring and adding the contributions of different projections to BP(RANDOMU(seed)−0.5), where BP represents back projection. In this way, an individual voxel may be examined for statistically significant deviation from a mean value, indicative of an anomalous or erroneous condition during reconstruction.

Specifically, the variance may be estimated by a double summation, with an inner summation over all pixels in a given view (for a given measurement) and with an outer summation over all views:

$$\text{var} = \sum_{\alpha} \sum_{i} (H_{\alpha i} M_i)^2.$$

The variance may also be estimated by reversing the order of the summations. Either way, the ICDF is then computed as the normalized quantity $$ICDF = \frac{BP(MCDF - 0.5)}{\sqrt{\text{var}}},$$

where var is the estimated variance. Under the null hypothesis of a random MCDF (correct data model), the ICDF has unit variance and is distributed normally due to the central limit theorem.

The ICDF exhibits spatial correlations among voxel values, because a back projection results in correlation between neighboring voxels. This is fundamentally due to the lack of a one-to-one relationship between image space and data (projection) space.

With the computation of the ICDF, an individual voxel (or pixel, e.g., in the case of a 2D slice) may be examined to determine if a data model is correct. Specifically, the ICDF indicates the number of standard deviations associated with each voxel in the image (e.g., voxel in a 3D image or pixel in a 2D slice). The ICDF output (values of the ICDF for respective voxels, e.g., pixels of a 2D slice) is provided to the display (output port) 130 by the ICDF module 140. Anomalies in the image reconstruction process may be detected based on observation of the voxels or pixels.

Figure 4:
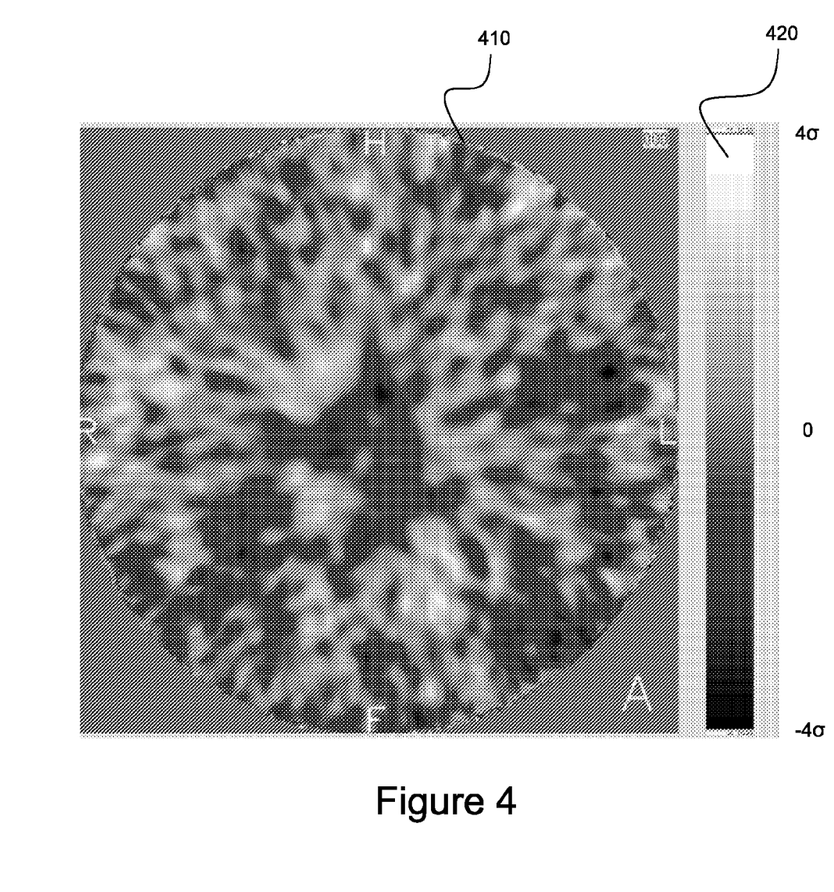
FIG. 4 is a plot of a two dimensional (2D) slice of ICDF data in a case of a random MCDF.

FIG. 4 is a plot of a two dimensional (2D) slice of ICDF data in a case of a random MCDF. A 2D slice 410 includes a plurality of pixels in a region of interest depicted as a disk in FIG. 4. In FIG. 4 as well as in FIGS. 5-6 described further below, left, right, head direction, feet direction, and anterior are labeled as "L", "R", "H", "F", and "A", respectively, to indicate the orientation of slices. Spatial correlations between the pixels are evident in FIG. 4, as the pixels within the disk exhibit more structure than the uncorrelated noise at the corners of FIG. 4 outside the disk. The pixels in slice 410 have intensities depicting ICDF values in the range from −4 to 4 standard deviations (−4σ to 4σ), as shown by the legend 420 that may be displayed along with slice 410. In some embodiments, the pixel intensities are displayed according to a color map to facilitate visual detection of anomalies by a human. In some embodiments, a lightest color (as perceived by the human eye) corresponds to a highest (or lowest) ICDF value, and a darkest color corresponds to a lowest (or highest) ICDF value. In this manner, a human may look at slice 410 and quickly deduce that no anomalies are detected by the ICDF technique. To be precise, one may deduce that either the data model is correct or the data is not sensitive enough to reveal the presence of a model error. In this sense, detected anomalies are indicative of model errors but the lack of detected anomalies is suggestive (but not dispositive) of the absence of model errors.

In some embodiments, an automatic determination is made, based on the ICDF, as to whether the image object satisfies a predetermined quality control criterion. For example, the pixels in a slice may be evaluated to determine whether any pixel has an ICDF value exceeding a predetermined threshold in magnitude, e.g., is more than three standard deviations (or some other number) from the mean. For example, because each pixel has an ICDF value corresponding to a number of standard deviations, a pixel that represents more than S standard deviations in magnitude may be flagged as an anomaly or possible anomaly, where S is a positive number. The zero-mean and unit-variance characteristics of the ICDF may also be tested automatically for quality control.

Figure 5:
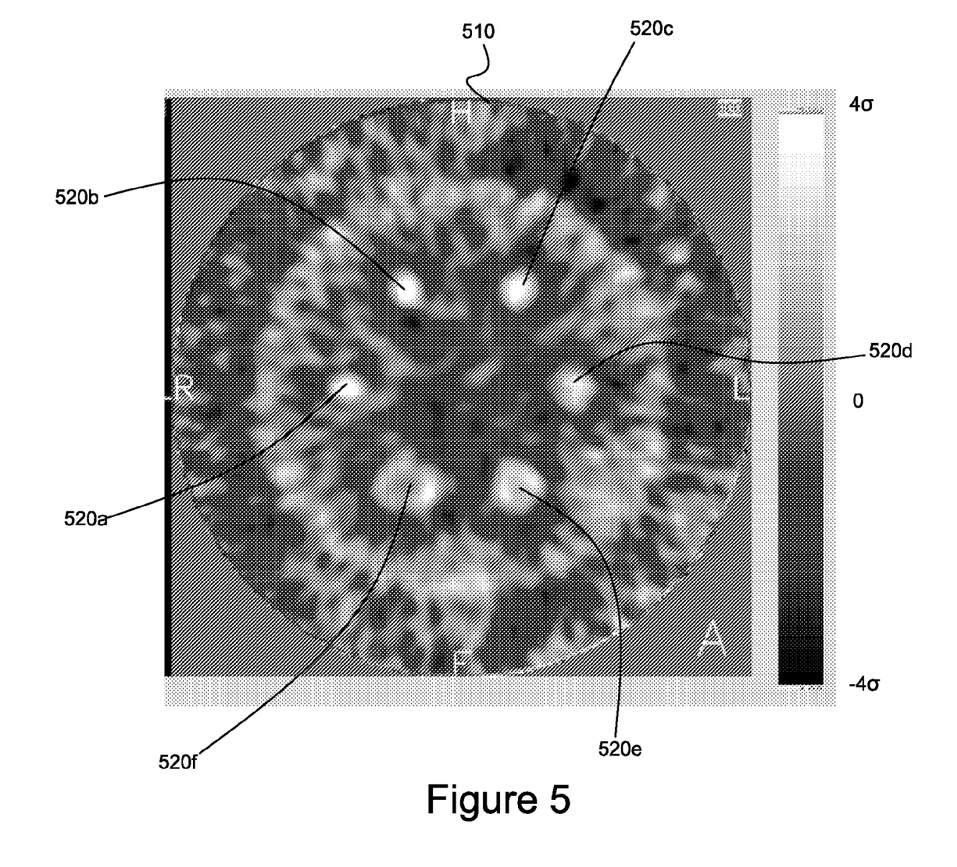
FIG. 5 is a plot of a 2D slice of ICDF data in a case of a non-random MCDF.

FIG. 5 is a plot of a 2D slice of ICDF data in a case of a non-random MCDF. In slice 510, regions 520a, 520b, 520c, 520d, 520e, and 520f of high ICDF values (e.g., exceeding a predetermined threshold) may be identified, indicating that the null hypothesis is violated, i.e., indicating a non-random MCDF. In other words, one may deduce that an error of some sort occurred during reconstruction.

Figure 6:
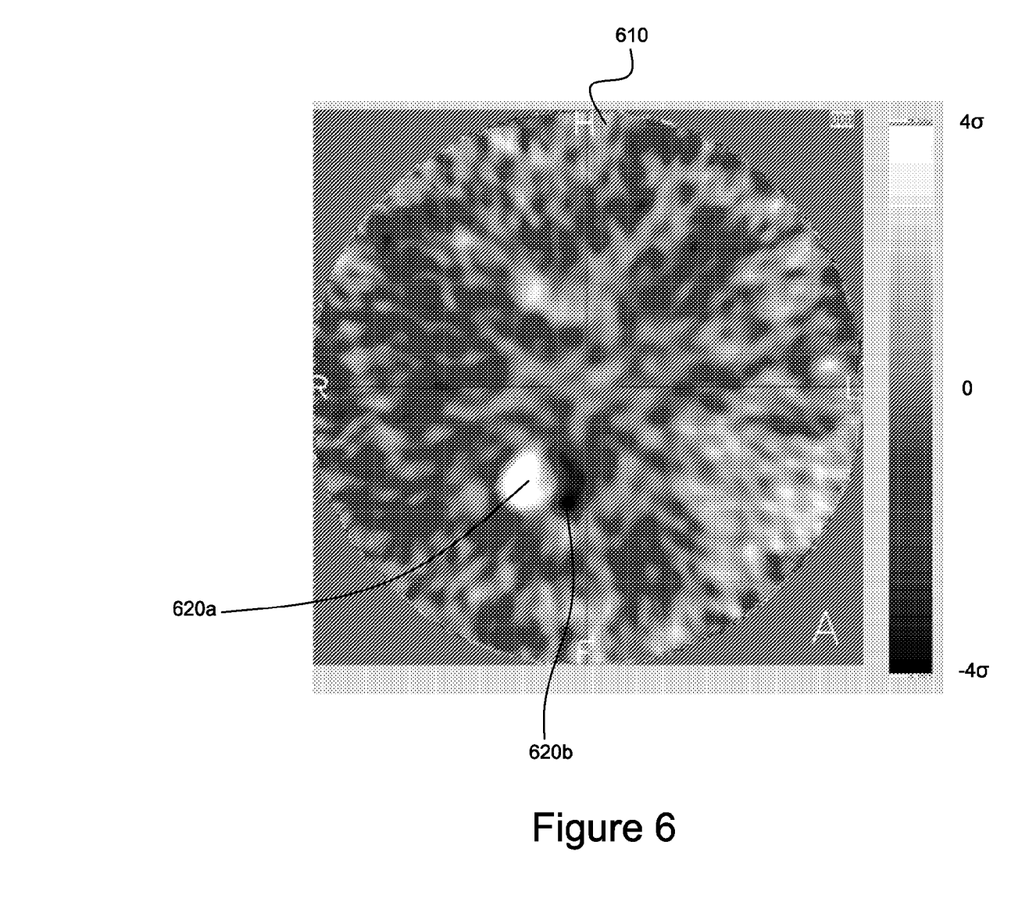
FIG. 6 is a plot of a 2D slice of ICDF data in another case of a non-random MCDF.

FIG. 6 is a plot of a 2D slice of ICDF data in another case of a non-random MCDF. In slice 610, regions 620a and 620b of high and low ICDF values, respectively may be identified, indicating that the null hypothesis is violated. This example shows that ICDF values at either end of the spectrum may be displayed for easy visual detection by a human and may be the basis of a determination of a model error.

Based on a determination of a model error, one may adjust a reconstruction process to correct the image object. Because a model error may be due to a number of factors, the adjustment(s) needed in various cases may vary in nature.

The reconstruction unit 120 and ICDF module 140 may be implemented in software and results obtained therefrom may be presented to a user on display 130, which may be a monitor or other display device. In some embodiments, processed results (e.g., one or more 2D slices of pixel data, or a 3D rendering of the image object I with ICDF output) may be presented to a user via a graphical user interface (GUI) on display 130. As mentioned previously, FIG. 1 illustrates one example of an architecture of a computer system 150 configured to implement such processing. As illustrated in FIG. 1, computer system 150 may include one or more processors 156. The processor 156 is connected to a communication infrastructure 154 (e.g., a communications bus, cross-over bar, or network). Computer system 150 may include a display interface 160 that forwards graphics, text, and/or other data from the communication infrastructure 154 (or from a frame buffer not shown) for display on the display unit 130.

Computer system 150 also includes a computer readable storage medium such as a memory module 158, which may include a main memory (such as a random access memory (RAM)) and/or a secondary memory, which are not shown for convenience but which are well known in the art. Secondary memory in the memory module 158 may include, for example, a hard disk drive (HDD) and/or removable storage unit(s), such as a floppy disk, magnetic tape, optical disk, flash memory, etc. The memory module 158 would be configured with appropriate interface for receiving the removable storage unit(s) and read from and/or write to the removable storage unit(s).

According to an embodiment, the computer readable storage medium of the computer system 150 tangibly embodies a program of instructions (i.e. computer program codes) executable by the one or more processors 156. When executed by the one or more processors 156, the program of instructions cause the one or more processors 156 to perform the processes described in FIGS. 2 and 3. The program of instructions can be embodied in the computer readable storage medium as a firmware in a non-removable storage medium or a software in removable storage medium.

Computer system 150 may also include a communications interface 152. Communications interface 152 allows software and data to be transferred between computer system 150 and external devices, e.g., to receive data D from imaging detector 110. Examples of communications interface 152 may include a modem, Ethernet card, wireless network card, a Personal Computer Memory Card International Association (PCMCIA) slot and card, or the like. Software and data transferred via communications interface 152 may be in the form of signals, which may be electronic, electromagnetic, optical, or the like that are capable of being received by communications interface 154. These signals may be provided to communications interface 154 via a communications path (e.g., channel), which may be implemented using wire, cable, fiber optics, a telephone line, a cellular link, a radio frequency (RF) link and other communication channels.

In an embodiment implemented using software, the software may be stored in a computer program product and loaded into computer system 150 using a removable storage drive or hard drive of memory 158, or using communications interface 152. The software, when executed by processor 156, causes the processor 156 to perform the functions of the methods described herein. In another embodiment, methods may be implemented primarily in hardware using, for example, hardware components such as a digital signal processor comprising application specific integrated circuits (ASICs). In yet another embodiment, methods are implemented using a combination of both hardware and software.

Although examples are illustrated and described herein, embodiments are nevertheless not limited to the details shown, since various modifications and structural changes may be made therein by those of ordinary skill within the scope and range of equivalents of the claims.

What is claimed is:

1. A method for quality control in image space for processing with an input data set, the method performed on a processor comprising:
   providing an image object and the input data set, the image object including a plurality of voxels;
   determining a data model from the image object;
   determining a cumulative distribution function (CDF) for the input data set from the data model and the input data set based on a plurality of projections;
   transforming the CDF to an image cumulative distribution function (ICDF) in image space, the ICDF representing a number of standard deviations associated with each voxel of the image object; and
   displaying an output of the ICDF.

2. The method of claim 1, wherein the image object is a three dimensional (3D) image object.

3. The method of claim 1, wherein the image object is a two dimensional (2D) image object.

4. The method of claim 1, wherein the CDF is a modified Poisson cumulative distribution function (MCDF).

5. The method of claim 1, wherein displaying the output of the ICDF includes displaying a slice of the output of the ICDF as a plurality of pixels, each pixel representing an ICDF value of a corresponding voxel of the image object.

6. The method of claim 5, wherein the slice is a two dimensional (2D) slice.

7. The method of claim 5, wherein displaying the slice includes displaying the ICDF in color with a plurality of colors representing a plurality of values of respective pixels.

8. The method of claim 5, further including automatically determining whether the image object satisfies a predetermined quality control criterion based on the ICDF.

9. The method of claim 8, wherein automatically determining whether the image object satisfies the predetermined quality control criterion includes determining whether any pixel has an ICDF value exceeding a predetermined threshold in magnitude.

10. The method of claim 8, wherein automatically determining whether the image object satisfies the predetermined quality control criterion includes automatically comparing a magnitude of an average ICDF value of the pixels to a predetermined mean threshold.

11. The method of claim 8, wherein automatically determining whether the image object satisfies the predetermined quality control criterion includes automatically comparing a variance of ICDF values of the pixels to a predetermined variance threshold.

12. The method of claim 1, wherein transforming the CDF to the ICDF comprises:
de-meaning the CDF;
back projecting the de-meaned CDF to image space; and
normalizing the back projected de-meaned CDF to unit variance.

13. The method of claim 12, wherein normalizing the back projected de-meaned CDF comprises:
computing amounts contributed by respective projections to a back projection of a uniform distribution function;
adding squared amounts contributed by respective projections to estimate a total variance; and
dividing the back projected de-meaned CDF by a square root of the estimated total variance.

14. The method of claim 13, wherein under a null hypothesis for the data model, the uniform distribution function is uniformly distributed between −0.5 and 0.5.

15. A nuclear imaging device for providing quality control in image space for processing with an input data set, the device comprising:
a detector unit configured to detect radiation emitted from within a detecting area and provide an input data set indicative of the detected radiation;
a tomographic reconstruction unit configured to provide an image object using the input data set, the image object including a plurality of voxels;
an image cumulative distribution function (ICDF) module configured to transform a cumulative distribution function (CDF) for the input data set in data space to an image cumulative distribution function (ICDF) in image space, the ICDF representing a number of standard deviations associated with each voxel of the image object; and
an output port configured for outputting the image object and the ICDF.

16. The nuclear imaging device of claim 15, wherein the image object is a three dimensional (3D) image object.

17. The nuclear imaging device of claim 15, wherein the CDF is a modified Poisson cumulative distribution function (MCDF).

18. The nuclear imaging device of claim 15, wherein the output port is configured to display a slice of the ICDF output as a plurality of pixels, each pixel representing an ICDF value of a corresponding voxel of the image object.

19. The nuclear image device of claim 15, wherein the ICDF module is further configured to automatically determine whether the image object satisfies a predetermined quality control criterion based on the ICDF.

20. The nuclear imaging device of claim 15, wherein the ICDF module is configured to transform the CDF to the ICDF by:
de-meaning the CDF;
back projecting the de-meaned CDF to image space; and
normalizing the back projected de-meaned CDF to unit variance.

21. The nuclear imaging device of claim 15, wherein the detector unit includes a single photon computed tomography detector.

22. The nuclear imaging device of claim 15, wherein the detector unit includes a positron emission tomography detector.

23. A computer readable non-transitory storage medium having instructions tangibly embodied thereon, the instructions when executed by a computer processor causing the processor to perform the operations of:
providing an image object and an input data set, the image object including a plurality of voxels;
determining a data model from the image object;
determining a cumulative distribution function (CDF) for the input data set from the data model and the input data set based on a plurality of projections;
transforming the CDF to an image cumulative distribution function (ICDF) in image space, the ICDF representing a number of standard deviations associated with each voxel of the image object; and
displaying an output of the ICDF.

* * * * *